(12) United States Patent
Borgese et al.

(10) Patent No.: US 12,186,442 B2
(45) Date of Patent: Jan. 7, 2025

(54) STERILIZATION MACHINE FOR THE STERILIZATION OF CAPS

(71) Applicant: SIDEL PARTICIPATIONS, Octeville-sur-Mer (FR)

(72) Inventors: Rossana Borgese, Parma (IT); Mattia Cenci, Parma (IT); Stefano Bernini, Parma (IT)

(73) Assignee: SIDEL PARTICIPATIONS, Octeville-sur-Mer (FR)

( * ) Notice: Subject to any disclaimer, the term of this patent is extended or adjusted under 35 U.S.C. 154(b) by 267 days.

(21) Appl. No.: 17/744,991

(22) Filed: May 16, 2022

(65) Prior Publication Data

US 2022/0362423 A1   Nov. 17, 2022

(30) Foreign Application Priority Data

May 17, 2021   (IT) .......................... 102021000012662

(51) Int. Cl.
*A61L 2/00*   (2006.01)
*A61L 2/18*   (2006.01)
(Continued)

(52) U.S. Cl.
CPC .............. *A61L 2/186* (2013.01); *B60L 13/10* (2013.01); *B61B 13/08* (2013.01);
(Continued)

(58) Field of Classification Search
CPC .............. A61L 2/186; A61L 2202/122; A61L 2202/14; A61L 2202/23; B61B 13/08; A60L 13/10
(Continued)

(56) References Cited

U.S. PATENT DOCUMENTS

| 3,905,317 A | * | 9/1975 | Pacilio | A61L 2/24 422/40 |
| 2008/0225248 A1 | * | 9/2008 | Poon | G03F 7/70341 355/53 |
| 2011/0142731 A1 | * | 6/2011 | Beckmann | B67B 3/003 422/292 |

FOREIGN PATENT DOCUMENTS

| EP | 0529157 A1 |   | 3/1993 |   |
| EP | 2500296 A1 | * | 9/2012 | ........... B65G 47/088 |

(Continued)

OTHER PUBLICATIONS

English Machine Translation of the Description Section of EP 2 500 296 A1 (Year: 2012).*

(Continued)

*Primary Examiner* — Monzer R Chorbaji

(57) ABSTRACT

A sterilization machine for the sterilization of caps, comprising an isolation chamber having an inner space in which the caps are advanced along a conveying path and separating the inner space from an outer space, a plurality of carts positioned within the inner space and an actuation unit arranged in the outer space and configured to selectively advance the carts along an advancement path by means of the generation of an electromagnetic field. Each cart comprises a pusher element configured to interact with a group of caps having one or more caps, to advance the respective group along the conveying path during the advancement of the respective cart along at least one portion of the advancement path. The actuation unit is configured to selectively lift the carts by means of levitation and to advance the carts along the advancement path by means of control of the electromagnetic field.

16 Claims, 3 Drawing Sheets

(51) Int. Cl.
  *B01J 19/00* (2006.01)
  *B60L 13/10* (2006.01)
  *B61B 13/08* (2006.01)
(52) U.S. Cl.
  CPC ..... *A61L 2202/122* (2013.01); *A61L 2202/14* (2013.01); *A61L 2202/23* (2013.01)
(58) Field of Classification Search
  USPC .......................... 422/1, 26, 28, 32, 291, 302
  See application file for complete search history.

(56) References Cited

FOREIGN PATENT DOCUMENTS

EP          3670404 A1    6/2020
WO    2015/128113 A1    9/2015

OTHER PUBLICATIONS

English Machine Translation of the Claims Section of EP 2 500 296 A1.*
Search Report dated Feb. 2, 2022.

* cited by examiner

STERILIZATION MACHINE FOR THE STERILIZATION OF CAPS

FIELD OF INVENTION

The present invention relates to a sterilization machine for caps, in particular caps for receptacles, even more in particular caps for bottles.

BACKGROUND

The sterilization of materials required for the packaging of products, such as, for example, food products, is of fundamental interest to guarantee the necessary shelf-life of the products packaged and, consequently, to ensure consumers' safety. This is even more important when the food products are packaged in aseptic conditions.

Filling of receptacles, such as containers, cans and bottles made of base components such as glass, plastic, aluminium, steel and composite materials, with any type of pourable food product, such as carbonated liquids (e.g., sparkling water, soft drinks and beer), non-carbonated liquids (including still water, fruit juices, tea, sports drinks, wine, milk, flavoured water, etc.) and drinks containing pulp is known.

In general, before being filled with the pourable food product, the receptacles are sterilized in a receptacle sterilization device and are subsequently filled with the desired pourable food product in a filling machine.

After filling of the receptacles, typically, the respective openings of the receptacle through which filling takes place are closed by means of the application of respective caps.

Before application, the caps are also sterilized in a respective sterilization machine. After sterilization, the sterile caps are fed to a capping machine, which also receives the filled receptacles.

A typical cap sterilization machine comprises a conveying device with a guide rail housed in an isolation chamber. The caps are positioned in succession and in contact with one another on the guide rail and by means of a pusher element, such as an insertion star, the caps are inserted one at a time and placed in contact with the succession of caps already present within the guide rail. This leads to a thrust force being exerted on the succession of caps, which results in the advancement of the succession of caps.

A disadvantage of these known sterilization machines lies in the impossibility of adapting the related operating speed as a function of the working conditions of the capping machines.

A further problem of these known sterilization machines is that due to the high temperatures, in combination with the contact between all the caps, to which the caps are exposed and to the contact between the caps, the caps are susceptible to deformations due to the forces acting within the succession of caps.

SUMMARY OF INVENTION

Therefore, with particular reference to EP 3 670 404 A1, the Applicant has developed an alternative sterilization machine, which is based on a conveying device, which comprises a guide rail arranged inside an isolation chamber and an endless rail, which carries a plurality of groups of moving carts. Each group of carts is operatively coupled to a respective pusher element, which is designed to interact with a respective group of a limited number of caps arranged on the guide rail in such a manner to advance the respective group.

In one embodiment, the endless rail is arranged under the isolation chamber and each moving cart is provided with a first interaction member. Furthermore, the conveying device comprises a plurality of auxiliary carts arranged inside the isolation chamber and coupled movably on a guide. Each auxiliary cart is associated with a respective cart and comprises a respective second interaction element configured to magnetically interact with the respective first interaction element in such a manner to transfer the advancement of the respective cart to an advancement of the auxiliary cart.

Furthermore, it should be noted that to guarantee the hygiene inside the isolation chamber, the auxiliary carts are arranged in an auxiliary chamber which in turn is arranged inside the isolation chamber. However, in this way, the mechanical complexity of the sterilization machine is increased.

Furthermore, it has been observed that the interaction between the auxiliary carts and the guide causes the formation of detritus, in particular inside the auxiliary chamber.

The object of the present invention is to produce a cap sterilization machine, which allows at least one of the aforementioned drawbacks to be overcome in a simple and economical manner.

The aforesaid object is achieved by the present invention, as it relates to a sterilization machine as defined in the independent claim 1. Alternative embodiments are protected by the dependent claims.

BRIEF DESCRIPTION OF THE DRAWINGS

For a better understanding of the present invention, embodiments thereof are described below, purely by way of non-limiting example and with reference to the accompanying drawings, wherein.

DETAILED DESCRIPTION

Figure 1:
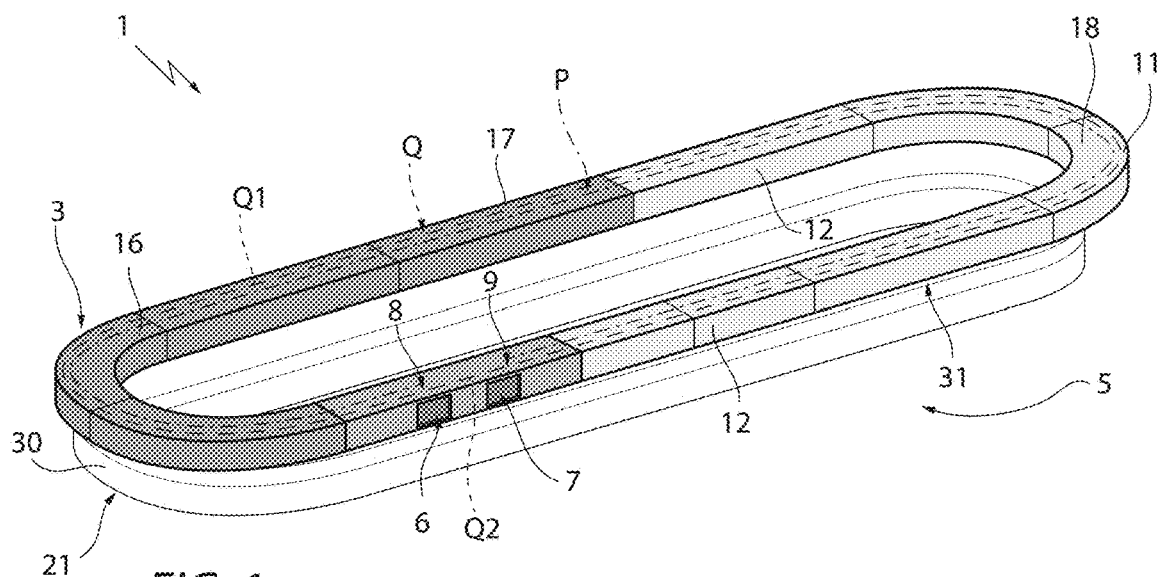
FIG. 1 illustrates, schematically and in a top view, a sterilization machine for caps according to a first embodiment of the present invention, with parts removed for clarity.

With reference to FIG. 1, a sterilization machine for the sterilization of caps 2 is indicated as a whole with 1.

In particular, the sterilization machine 1 is configured to sterilize caps 2 that can be applied to receptacles, such as, for example, bottles, containers or the like, containing a pourable food product.

The receptacles can be made of a thermoplastic polymer such as, for example, polyethylene terephthalate. Additionally, or alternatively, the receptacles can also be made of a different material such as, for example, glass, a metal material, a composite material, a multi-layer material and the like.

In more detail, the pourable products can, for example, be carbonated liquids (such as sparkling water, soft drinks and beer), non-carbonated liquids (such as still water, fruit juices, wine, tea, milk, flavoured water), emulsions, suspensions, high viscosity liquids and drinks containing pulp.

According to some embodiments, the caps 2 can be made of polymeric material, such as polyethylene, in particular high-density polyethylene.

Alternatively or additionally, the caps 2 can vary in format (for example, in their extension—height, diameter, etc.) and/or in their type. For example, the caps 2 can comprise an internal thread to be screwed onto the receptacles. In particular, the caps 2 can be of the "sports cap" or "screw cap" type.

With particular reference to FIG. 1, the sterilization machine 1 comprises an isolation chamber 3 having an inner space 4 in which the caps 2 are advanced along a conveying path P.

Moreover, the isolation chamber 3 separates the inner space 4 from an outer space 5.

Additionally, the sterilization machine 1 can comprise a conditioning device configured to control the physical and/or chemical conditions in the inner space 4. The machine is in this way configured so that the inner space is aseptic and/or sterile. For example, the conditioning device can be configured to control the temperature, pressure, humidity, sterility and/or the chemical composition in the inner space and/or to control the flow of gases present in the inner space 4.

Preferably, the conditioning device can be configured to control the physical and/or chemical conditions in the inner space 4 locally; i.e., the physical and/or chemical conditions can vary in different portions of the inner space 4.

Advantageously, the conditioning device can be configured to maintain an aseptic condition in the inner space 4.

In more detail, the isolation chamber 3 can comprise an inlet 6 for the caps 2 to be sterilized and an outlet 7 for the sterilized caps 2.

In particular, the conveying path P extends between a start station 8 (being arranged substantially at the inlet 6) and an end station 9 (being arranged substantially at the outlet 7). In particular, in use, the caps 2 advance from the start station 8 to the end station 9. More specifically, the caps 2 are, in use, sterilized during their advancement along the conveying path P (i.e., during their advancement from the start station 8 to the end station 9).

With particular reference to FIG. 1, the isolation chamber 3 can have an annular configuration; i.e., the inner space 4 can be annular.

Preferably, the isolation chamber 3 can comprise a plurality of walls that delimit the inner space 4.

Operatively, this plurality of walls comprises a lower wall 10 and an upper wall 11. These lower 10 and upper 11 walls are operatively distanced from one another along a vertical axis A. These upper 11 and lower 10 walls are transversal to this vertical axis A. This vertical axis A is operatively parallel to gravity.

This plurality of walls comprises two lateral walls 12. These two lateral walls 12 are operatively distanced from one another along a horizontal axis B. These lateral walls 12 are transversal to this horizontal axis B. This horizontal axis B is operatively transversal to gravity.

According to some non-limiting embodiments, the sterilization machine 1 can comprise at least one guide rail (not illustrated and known per se) arranged in the inner space 4 and configured to support the caps 2 during their advancement along the conveying path P. In particular, the guide rail determines the conveying path P.

More specifically, the guide rail can comprise rectilinear portions and curved portions that respectively define rectilinear portions and curved portions of the conveying path P.

Moreover, the guide rail comprises at least an inlet section, in particular arranged substantially at the start station 8, and an output section, in particular arranged substantially at the end station 9, to respectively allow the caps 2 to be fed to the guide rail and these caps 2 to exit from the guide rail.

According to some embodiments, the isolation chamber 3, in particular the inner space 4, can comprise a plurality of zones defined as a function of the operations to which the caps 3 are exposed while being conveyed through the respective zones.

For example, the conditioning device comprises a sterilizer configured to inject a sterilizing fluid (such as hydrogen peroxide and/or any other chemical sterilizing agent in gaseous, vapour and/or liquid form) into an injection zone 16 of the isolation chamber 3, in particular of the inner space 4. In particular, during the advancement of the caps 2 through the injection zone 16, the caps 2 are, in use, exposed to the sterilizing fluid, which deposits on the caps 2.

Moreover, the isolation chamber 3, in particular the inner space 4, can also comprise a contact and/or activation zone 17. The contact zone 17 is arranged downstream of the injection zone 16 along the conveying path P. In particular, during the advancement of the caps 2 in the contact zone 17, the sterilizing fluid acts on the caps 2.

Preferably, the isolation chamber 3, in particular the inner space 4, can also comprise a ventilation zone 18 arranged downstream of the contact zone 17 along the conveying path P. In particular, in use, while the caps 2 are being conveyed through the ventilation zone 18 the sterilizing fluid present on the caps 2 evaporates from the caps 2.

Preferably, the conditioning device can comprise a ventilation unit coupled to the ventilation zone 18 to allow the necessary ventilation of the ventilation zone 18.

Figure 2:
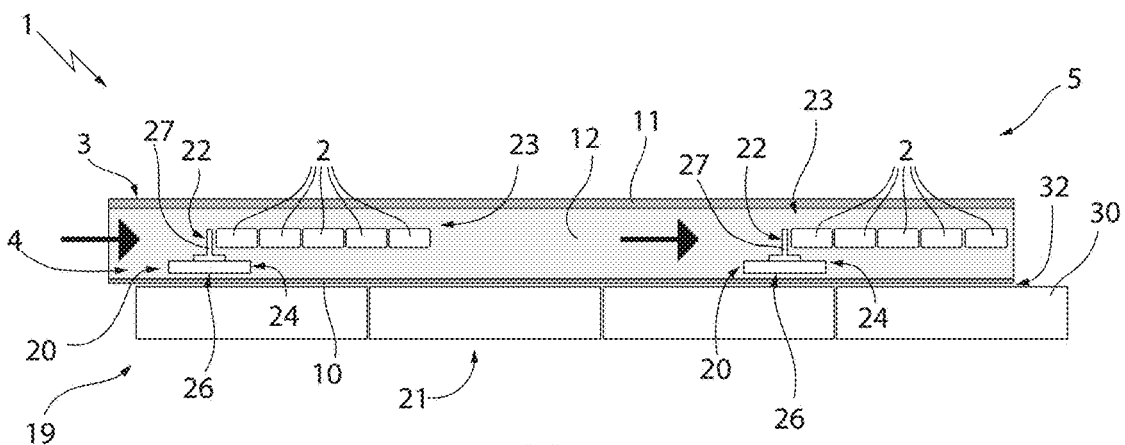
FIG. 2 illustrates, in a schematic side and sectional view, a portion of the sterilization machine of FIG. 1, with parts removed for clarity.
Figure 3:
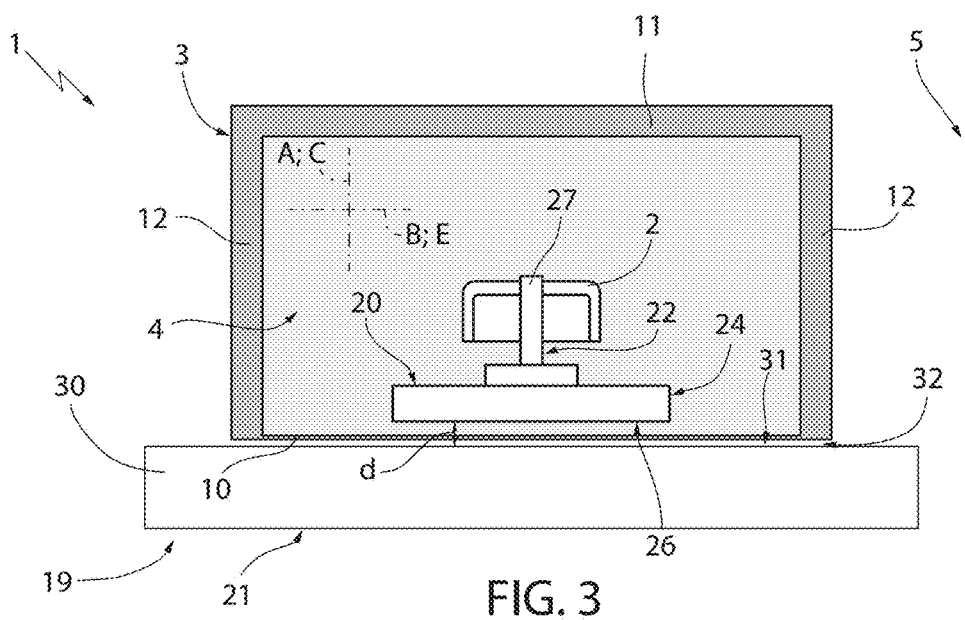
FIG. 3 illustrates, in a schematic front and sectional view, a detail of the sterilization machine of FIG. 2, with parts removed for clarity.
Figure 4:
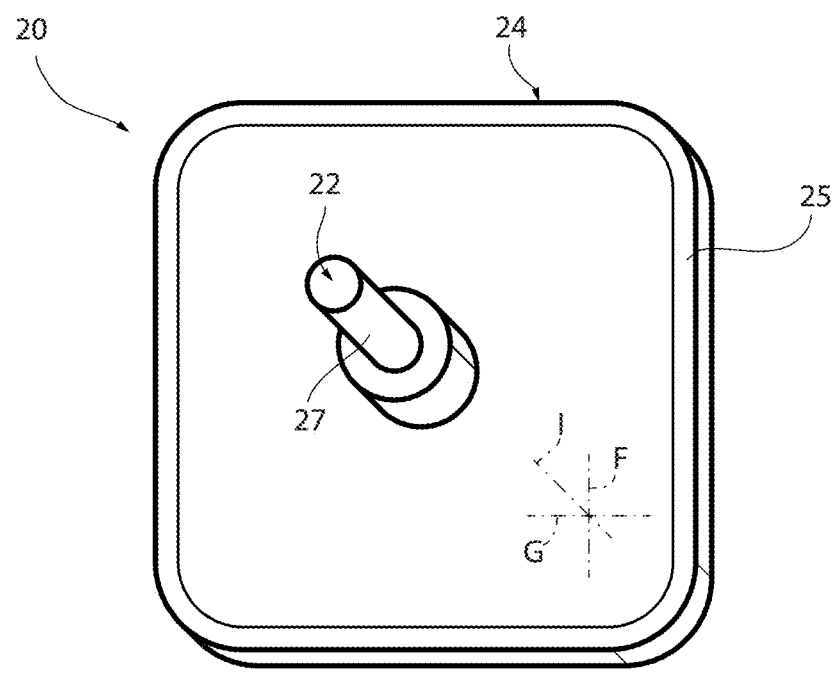
FIG. 4 illustrates, in a schematic view, a detail of the sterilization machine of FIG. 1, with parts removed for clarity.

With particular reference to FIGS. 2 to 4, the sterilization machine 1 comprises a conveying device 19 configured to implement and control the advancement of the caps 2 along the conveying path P.

In more detail, the conveying device 19 comprises:
a plurality of carts 20 positioned within the inner space 4; and
an actuation unit 21 arranged in the outer space 5 and configured to selectively advance the carts 20 along an advancement path Q by means of the generation and control of an electromagnetic field, in particular along an endless or and/or annular advancement path Q.

Figure 6:
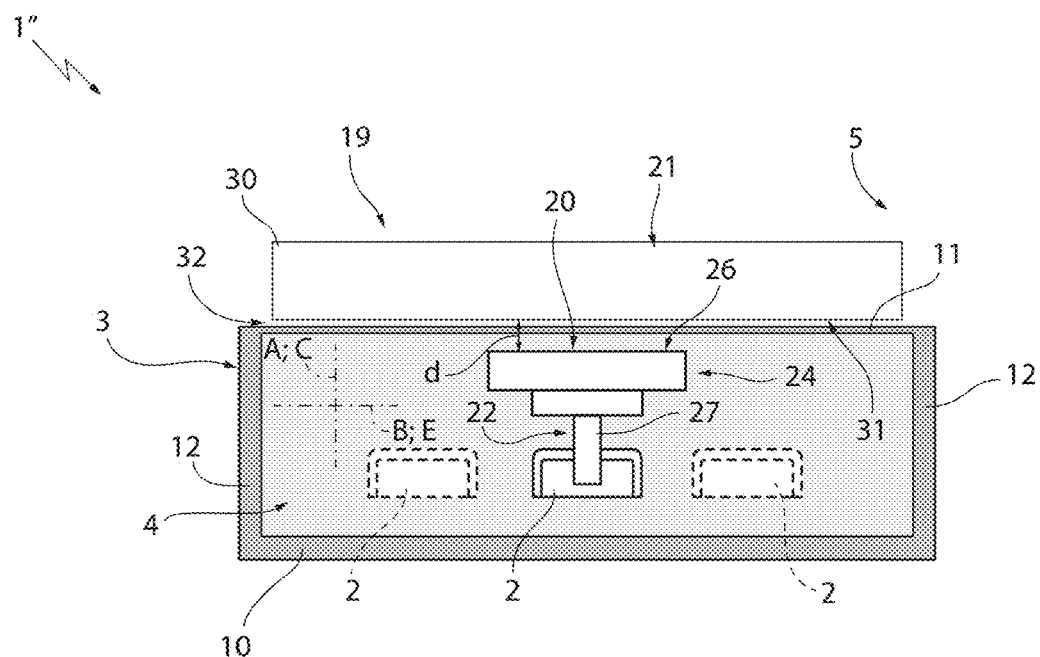
FIG. 6 illustrates, in a schematic front and sectional view, a detail of a sterilization machine according to a third embodiment of the present invention, with parts removed for clarity.

At least one wall of the chamber 3 is spatially interposed between the actuation unit 21 and the inner space 4. This interposed wall could be the lower wall 10, for example as shown in FIG. 3, or the upper wall 11, for example as shown in FIG. 6.

With particular reference to FIGS. 2 to 4, each cart 20 comprises at least one pusher 22. For each cart 20, the machine 1 is configured so that the pusher 22 interacts with and/or pushes a respective group 23 of caps 2, such that, by means of advancement of the cart 20 along at least one portion Q1 of the advancement path Q, the group 23 advances along the conveying path P. For each cart 20, the machine 1 is configured such that, by means of a pushing action exerted by the pusher 22 on the respective group 23, the advancement of the cart 20 along at least one portion Q1 of the advancement path Q corresponds to the advancement of the group 23 along the conveying path P. For each cart 20, the machine 1 is configured so that, by means of this pushing action, the advancement of the cart 20 along this at least one portion Q1 of the advancement path Q causes this advancement of the group 23 along the conveying path P. FIGS. 3, 5, 6 and 7 are to be considered lying on a plane locally perpendicular to the advancement path Q. FIG. 2 is to be considered lying on a plane parallel to a rectilinear section of the advancement path Q. For each cart 20, the actuation unit 21 is configured in such a manner to control the advancement of the cart 20 along the advancement path Q, by means of control of the electromagnetic field and independently from the other carts 20.

For each cart 20, the actuation unit 21 is configured in such a manner to control by means of magnetic levitation a first position component of the cart 20, independently from the other carts 20. This first position component is along a first direction C. This first position component is with respect to the actuation unit 21 and/or to the chamber 3. This first direction C is locally transversal and/or orthogonal to the advancement path Q. This first direction C lies locally on a plane that is transversal and/or orthogonal to the advancement path Q. The actuation unit 21 is configured to carry out this control of the first component during the advancement of the cart 20 along the advancement path Q.

For each cart 20, the actuation unit 21 is configured in such a manner to control, by means of control of the electromagnetic field and independently from the other carts 20, also a second position component of the cart 20 with respect to the actuation unit 21 and/or to the chamber 3. This second position component is along a second direction E. This second direction E is locally transversal and/or orthogonal to the advancement path Q and to the first direction C. This second direction E lies locally on the above-mentioned plane that is transversal and/or orthogonal to the advancement path Q. The actuation unit 21 is configured to carry out this control of the second component during the advancement of the cart 20 along the advancement path Q.

As can be seen in FIG. 3, the first direction C can be parallel to the vertical axis A. As can be seen in FIG. 3, the second direction E can be parallel to the horizontal axis B.

For each cart 20, the first position component could be considered an elevation or height of the cart 20 in the inner space 4.

For each cart 20, the second position component could be considered a lateral position of the cart 20 in the inner space 4.

In this way, the actuation unit 21 is configured to generate and control (regulate) the electromagnetic field that interacts selectively by means of electromagnetic forces with the carts 20, in such a manner to advance the carts 20 along the advancement path Q and simultaneously control the transversal position of the carts 20 along or on a plane transversal to the advancement path Q.

Due to the control of the elevation and/or of the lateral position by means of electromagnetic effect and/or by means of magnetic levitation, the cart 20 can have a simpler mechanical configuration, which reduces the risk of contamination and/or does not require the chamber 3 to be divided into several partial chambers.

The actuation unit 21 could be defined by a planar motor. A planar motor is particularly suitable to be controlled in such a manner to obtain the aforesaid effects of control of the first position component, of the second position component, and of the advancement of the carts 20.

In more detail, for each cart 20, the actuation unit 21 could be configured in such a manner to control the first position component maintaining the cart 20 distanced from the lower wall 10 and/or from the upper wall 11 of the chamber 3, independently from the other carts 20. The actuation unit 21 is configured to maintain the cart 20 distanced from the lower wall 10 or from the upper wall 11, independently from the other carts 20 and acting against gravity.

In this way, the cart 20 can be controlled in a very precise manner, so as to reduce the risk of interference between cart 20 and upper wall 11 and/or between cart 20 and lower wall 10. Moreover, the extension of the chamber 3 along the vertical axis A can be reduced due to the fact that the first position component can be controlled in a precise manner.

It should be noted that, without the control of the first position component, the carts 20 would fall as a result of gravity towards the lower wall 10, and/or could contact the lower wall 10 and/or the upper wall 11 as a result of disturbances.

The machine 1 can be configured to allow a user to set up in advance a desired value of this first position component as a function of the type of cap. A variation of the type of cap can cause a variation of the format and/or of other features of the cap. For each cart 20, the actuation unit 21 is configured to control in advance the first position component of the cart 20 as a function of the desired value set.

In this way, the user can intuitively and conveniently adapt the machine 1 to the specific type of cap, so as to improve the flexibility of the machine 1.

The control of the first position component is carried out in such a manner to pursue and/or maintain this set desired value of the first position component.

In this way, the actuation unit 21 is configured to generate and control (adjust) the electromagnetic field that selectively interacts by means of electromagnetic forces with the carts 20, in such a manner to advance the carts 20 along the advancement path Q and control the transversal position of the carts 20 along a plane transversal to the advancement path Q.

In particular, the actuation unit 21 can be configured to advance the carts 20 independently from one another by means of the generation and the control of the electromagnetic field. Even more in particular, the actuation unit 21 can be configured to accelerate and/or decelerate independently from one another the carts 20 and/or modify a positioning of the carts 20 independently from one another by means of the generation and the control of the electromagnetic field.

In more detail, for each cart, the actuation unit 21 could be configured in such a manner to control the second position component by maintaining the cart 20 distanced from the lateral walls 12 of the chamber 3. The actuation unit 21 is configured to maintain the cart 20 distanced from the lateral walls 12 independently from the other carts 20.

In this way, the above-mentioned in terms of control of the lack of interference between cart 20 and walls of the chamber 3 are further increased.

It should be noted that, in the absence of the control of the second position component, the carts 20 could contact one of the lateral walls 12 due to disturbances.

For each cart 20, the first position component can be defined by a distance d. The distance d is defined between the actuation unit 21 and the cart 20.

For each cart 20, the actuation unit 21 is configured to control the respective distance d.

Preferably, for each cart 20, the actuation unit 21 is configured to control the respective distance d such that the value of this distance d falls within the interval from 0.5 mm to 15.0 mm, in particular from 0.5 mm to 10.0 mm, or from 0.5 mm to 5 mm.

In this way the distance d is sufficient to avoid risks of interference due to disturbances between the cart 20 and the lower wall 10 or the upper wall 11 of the chamber 3, while at the same time also ensuring sufficient control of the actuation unit 21 on the advancement and on the above-mentioned position components of the cart 20.

In particular, during the advancement, the carts 20 advance without being in contact with one or more portions of the isolation chamber 3.

Therefore, by means of the control of the first position component of the carts 20 along the first direction C, the actuation unit 21 is configured to vertically control the carts 20 (i.e., the distance d) during their advancement, and consequently a respective distance between the carts 20 and the lower wall 10 and/or between the carts 20 and the upper wall 11. Moreover, by means of the control of the carts 20 along the second direction E, the actuation unit 21 is configured to control the carts 20 laterally or horizontally during their advancement.

Each cart 20 comprises a plate 24. The machine 1 is configured so that the actuation unit 21 interacts with the plate 24 through electromagnetic effect to control the advancement of the cart 20 along the advancement path Q and/or the first position component and/or the second position component.

This plate 24 presents a first extension along the advancement path Q. This first extension is along a first extension axis F indicated in FIG. 4. This first extension is a length of the cart 20.

The value of this first extension falls within the interval from 100 to 250 mm, so as to facilitate the control by electromagnetic effect of the pitching inclination of the cart 20 with respect to the need to maintain the dimensions of the cart 20 limited.

This plate 24 presents a second extension along this second direction E. This second extension can also be considered along a second extension axis G indicated in FIG. 4. This second extension is a width of the cart 20.

The value of this first extension falls within the interval from 100 to 250 mm, so as to facilitate the control by electromagnetic effect of the roll inclination of the cart 20 with respect to the need to maintain the dimensions of the cart 20 limited.

Moreover, the advancement path Q or said at least one portion Q1 of the advancement path Q, could comprise at least one rectilinear sector and at least one curved sector.

The actuation unit 21 is configured to control the electromagnetic field such as to modify and/or control the roll inclination and/or the pitching inclination of the cart during the advancement along the at least one curved sector. In this way, the effects of the centrifugal force can be offset. Moreover, the above-mentioned value of the first extension and/or the above-mentioned value of the second extension are chosen to facilitate in particular the control of the tilt along the at least one curved sector.

This plate 24 has a thickness along the first direction C. This thickness can be considered as a third extension along a third extension axis I. The third extension axis I is transversal to both the first extension axis F and the second extension axis G.

The value of said thickness falls within the interval from 0.8 to 1.5 mm, so as to obtain an excellent compromise between the need for sufficient electromagnetic interaction and the need to maintain a limited vertical footprint of the cart 20.

The machine 1 is void of a mechanical guide for guiding by means of mechanical contact the advancement of the carts 20 along the advancement path Q. In this way, the advancement path Q can be defined solely by the control of the electromagnetic field, so as to further simplify the mechanics of the machine 1, further limiting the risk of undesirable contaminations.

The machine can comprise a cooling device.

The isolation chamber 3 and the actuation unit 21 are distanced from one another along this first direction C so as to define an interspace 32 interposed between the isolation chamber 3 and the actuation unit 21. The cooling device is configured to generate a cooling flow in the and/or through the interspace 32. This cooling flow is produced by means of at least air and/or water and/or any other cooling fluid.

In this way, damage or excessive wear of the actuation unit 21 due to the heat released during sterilization is avoided.

More specifically, the caps 2 of each group 23 can be arranged in succession to one another.

In the specific case illustrated in FIG. 2, each group 23 can comprise five caps 2.

Preferably, each group 23 can comprise a number of caps whose value can fall between 1 and 20 or between 1 and 15.

In the specific case of FIG. 2, each group 23 comprises the same number of caps 2. However, the number of caps 2 of the groups 23 can, according to some embodiments, vary from one another.

In more detail, in use, by means of the advancement of the carts 20 along the advancement path Q, an advancement of the pushers 22, which in turn push the respective groups 23 along the conveying path P, is obtained.

Moreover, during the advancement of the carts 20 along the advancement path Q, the pushers 22 pass through the start station 8 and the end station 9. In particular, the end station 9 can be arranged downstream of the start station 8 along the advancement path Q.

In further detail, for each cart 20, the pusher 22 comes into contact cyclically with a respective group 23 at the start station 8 and detaches cyclically from the respective group 23 at the end station 9. During the advancement of the pusher 22 from the start station 8 to the end station 9, the pusher 22 is in contact with the group 23. During the advancement of the pusher 22 from the end station 9 to the start station 8, the pusher 22 is not in contact with any cap.

The machine 1 comprises at least a guide rail to guide by means of mechanical contact the advancement of the caps along the conveying path P. For each cart 20, the pusher 22 is engaged slidingly in the guide rail, to generate the aforesaid pushing action.

In particular, the advancement path Q can comprise an active portion Q1 and a return portion Q2. The active portion Q1 can be considered as corresponding to the aforesaid at least one portion of the advancement path Q, along which at least one portion Q1 produces the pushing effect of each cart 20 on the respective group 23. In particular, each cart advances along the active portion Q1 and the return portion Q2 when the respective pusher element 22 advances respectively from the start station 8 to the end station 9 and from the end station 9 and to the start station 8.

More specifically, the portion Q1 can be locally parallel to the conveying path P.

Moreover, the actuation unit 21 is configured to advance the carts 20 along the advancement path Q continuously so that the respective pushers 22 advance through the start station 8 and the end station 9 continuously; i.e., each time each pusher 22 passes through the start station 8, the pusher 22 comes into contact with a respective new group 23 to push the respective new group 23 towards the end station 9.

According to some non-limiting embodiments, the actuation unit 21 can be configured to modulate an advancement speed of the carts 20 by means of the control of the electromagnetic field, in particular as a function of the portion of the advancement path along which the carts 20 advance at a specific time. For example, the speed can be controlled as a function of the fact that the carts 20 advance along a portion that is in the injection zone 16 or in the contact or activation zone or in the ventilation zone.

For each cart 20, the base plate 24 supports the pusher 22.

In more detail, each base plate 24 comprises at least a magnetic or ferromagnetic portion to interact with the electromagnetic field.

Preferably, each base plate 24, in particular each external housing 25, can comprise a face 26 facing towards the wall 10 and/or towards the actuation unit 21.

With particular reference to FIGS. 2 to 4, in the specific case each pusher 22 comprises a bar 27 configured to contact and push the respective groups 23 along the conveying path P.

With particular reference to FIGS. 1 to 3, the actuation unit 21 can comprise a housing 30, a plurality of coils arranged in the housing 30 and a controller configured to selectively (electrically) supply the coils to create and control the electromagnetic field.

Preferably, the housing 30 has an annular shape. In particular, the coils are arranged along the whole of the extension of the housing 30.

More specifically, the housing 30 can comprise a face 31 facing towards the isolation chamber 3, in particular the lower wall 10 or the upper wall 11.

In particular, the lower wall 10 or the upper wall 11 is interposed between the housing 30 and the carts 20.

Preferably, the distance d between a cart 20 and the actuation unit 21 is defined by the distance between the respective faces 26 and 31, in particular with respect to an axis normal to the face 31.

In use, the sterilization machine 1 sterilizes the caps 2 while they are being conveyed within the inner space 4 and along the conveying path P.

In more detail, the operation of the sterilization machine 1 comprises at least the steps of:
 advancing the carts 20 along the advancement path Q; and
 pushing the groups 23 of caps 2 along the conveying path P due to the advancement of the carts 20 along the advancement path Q and the contact of the respective pusher 22 with the respective groups 23.

Additionally, the operation of the sterilization machine 1 can further comprise the steps of:
 feeding the caps 2 onto the guide rail at the start station 8; and/or
 unloading the caps 2 from the guide rail at the end station 9; and/or
 injecting the sterilizing fluid in the injection zone 16; and/or
 ventilating the ventilation zone 18.

Figure 5:
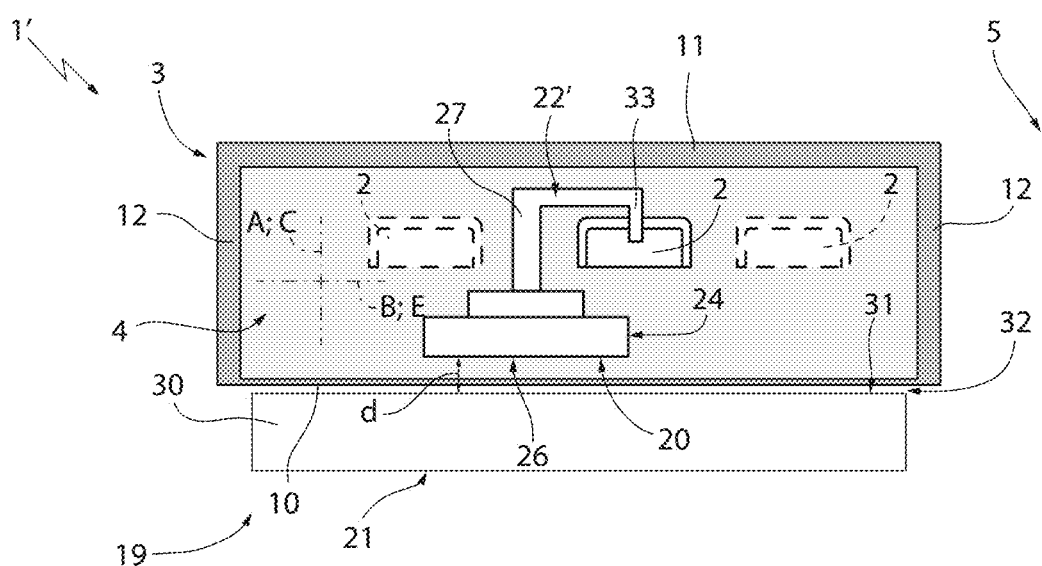
FIG. 5 illustrates, in a schematic front and sectional view, a detail of a sterilization machine according to a second embodiment of the present invention, with parts removed for clarity.

FIG. 5 illustrates a second embodiment of a machine according to the present description. The second embodiment is indicated with 1'.

The machine 1' comprises a plurality of guide rails distanced from one another and/or distributed along the second direction E. The second direction E can be parallel to the horizontal axis B. The guide rails are adapted to respective types of different caps. Each guide rail is configured to guide by means of mechanical contact, the advancement of the caps of the respective type along the conveying path P. The machine 1 is configured to allow a user to select in advance one of the guide rails as a function of the type of cap. For each cart 20, the actuation unit 21 is configured to control in advance the second position component of the cart 20 as a function of the guide rail selected.

During the advancement of the cart 20, the actuation unit controls the second position component in such a manner to pursue or maintain the controlled value of the second position component. This controlled value corresponds to the guide rail selected.

In the machine 1', for each cart 20, the bar 27 of the pusher can define a hooked end 33.

FIG. 6 illustrates a third embodiment 1" of a machine according to the present description.

The machine 1" differs from the machine 1' in that in the machine 1' the actuation unit 21 is located on the side of the lower wall 10, while in the machine 1" the actuation unit 21 is located on the side of the upper wall 11. Moreover, in the machine 1", for each cart 20, the bar 27 does not define the hooked end 33.

Figure 7:
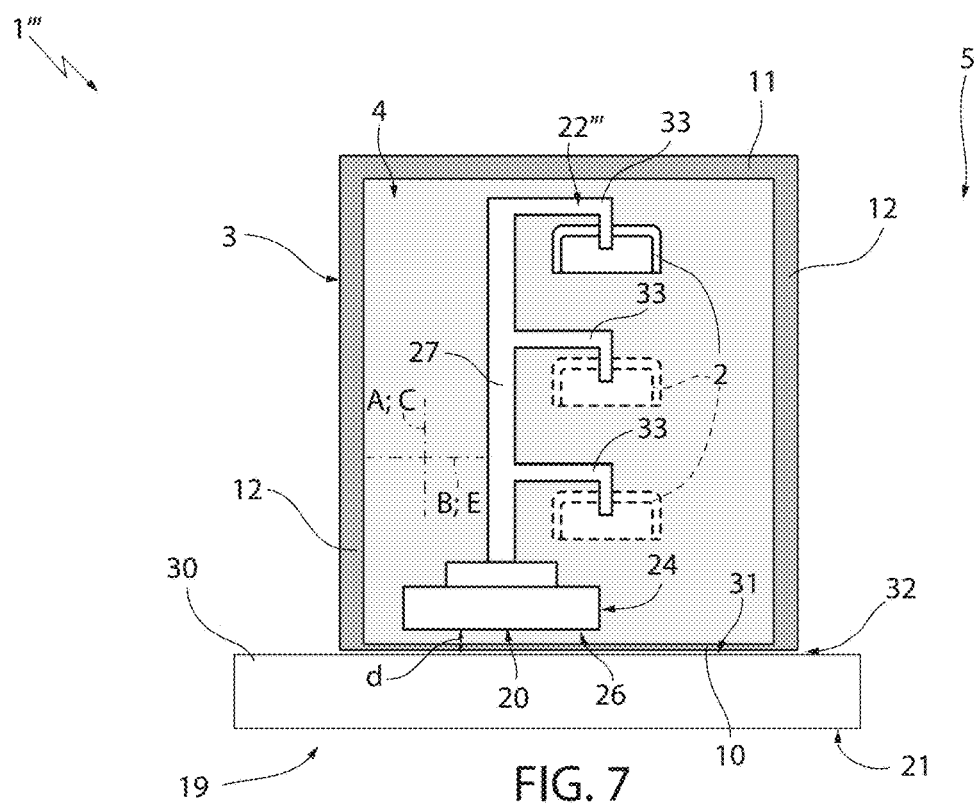
FIG. 7 illustrates, in a schematic front and sectional view, a detail of a sterilization machine according to a fourth embodiment of the present invention, with parts removed for clarity.

FIG. 7 illustrates a fourth embodiment 1''' of a machine according to the present description.

The machine 1''' comprises a plurality of guide rails distanced from one another and/or distributed along the first direction C. The first direction can be parallel to the vertical axis A. The guide rails are adapted to respective different types of caps. Each guide rail is configured to guide, by means of mechanical contact, the advancement of caps of the respective type along the conveying path P.

In the machine 1''', each cart 20 comprises a plurality of pushers 22''', each slidably engaged in a respective guide rail. In this way, the step of controlling in advance the first position component of the cart 20 as a function of the type of cap is not required.

A fifth embodiment, not shown, could differ from the machine 1''' in that the guide rails are distanced along the second direction E. This further embodiment, also comprising, for each cart, a plurality of pushers each slidably engaged in the respective guide, thus makes a step of controlling in advance the second position component of the cart 20 as a function of the type of cap unnecessary.

From an examination of the features of the sterilization machines 1, 1', 1" or 1''' according to the present invention the advantages that can be obtained therewith are evident.

In particular, the sterilization machines 1, 1', 1" and 1''' do not require a mechanical guide for the carts 20. This reduces the complexity and allows the formation of detritus caused by contact between the carts 20 and a mechanical guide to be avoided.

Moreover, the need to provide an auxiliary chamber in the chamber 3, to separate the zone in which the caps advance from other components that could be a source of contamination, is avoided.

A further advantage lies in the fact that the electromagnetic field acts directly on the carts 20 present in the inner space 4, which allows a further reduction of the complexity.

Finally, it is clear that modifications and variants can be made to the sterilization machine described and illustrated without departing from the scope of protection defined by the claims.

The invention claimed is:

1. A sterilization machine for the sterilization of caps comprising at least:
an isolation chamber having an internal space, the machine being configured such that the caps are advanced along a conveying path placed within the internal space and the isolation chamber separating the inner space from an outer space;
a plurality of carts positioned within the inner space; and
an actuation unit arranged in the outer space and configured to advance the carts along an advancement path by means of the generation of an electromagnetic field;
wherein each cart comprises at least one pusher configured to interact with a group of caps having one or more caps and such that the advancement of the carts along at least a portion of the advancement path corresponds to the advancement of the group along the conveying path, the at least one portion being arranged within the inner space;
wherein, for each cart, the actuation unit is configured to control the advancement of the cart along the advancement path, by means of control of the electromagnetic field and independently from the other carts;
wherein, for each cart independently advancing from the other carts, the actuation unit is configured to control by means of magnetic levitation a first position component of the cart with respect to the actuation unit, the first position component being along a first direction, the first direction being transversal to the advancement path;
wherein, for each cart advancing independently from the other carts, the actuation unit is configured to control, by means of the control of the electromagnetic filed, also a second position component of the cart with respect to the actuation unit, the second position component being along a second direction, the second direction being transversal with respect to the first direction and the advancement path.

2. The sterilization machine according to claim 1, wherein the isolation chamber comprises a plurality of walls delimiting the inner space;
the plurality of walls comprising a lower wall and an upper wall, the lower wall and the upper wall being distanced from one another along a vertical axis which is operatively parallel to the gravity, the lower wall and the second wall being transversal to the vertical axis;
the first direction is parallel to the vertical axis;
for each advancing cart, the actuation unit is configured to control the first position component maintaining the cart distanced from the lower wall or the upper wall of the isolation chamber, independently from the other carts and acting against the gravity.

3. The sterilization machine according to claim 1, wherein the machine is configured to allow a user to set up in advance a desired value of the first position component in function of the type of cap to be sterilized;
for each cart, the actuation unit is configured to control in advance the first position component of the cart as a function of the set desired value.

4. The sterilization machine according to claim 1, wherein:
for each cart, the first position component is defined by a distance between the actuation unit and the cart;
for each cart, the actuation unit is configured to control the respective distance such that the value of the distance falls within the interval from 0.5 mm to 15.0 mm, or from 0.5 mm to 10.0 mm, or from 0.5 mm to 5 mm.

5. The sterilization machine according to claim 1, wherein:
each cart comprises a plate, the machine being configured such that the actuation unit interacts by means of an electromagnetic effect with the plate for controlling the advancement of the cart along the advancement path and for controlling the first position component;
the plate presents a first extension along the advancement path;
the plate carries the respective pusher.

6. The sterilization machine according to claim 5, wherein the value of the first extension falls within an interval from 100 to 250 mm.

7. The sterilization machine according to claim 6, wherein:
the plate presents a second extension along the second direction;
the value of the second extension falling into an interval from 100 to 250 mm.

8. The sterilization machine according to claim 5, wherein:
the plate presents a second extension along the second direction;
the value of the second extension falling into an interval from 100 to 250 mm.

9. The sterilization machine according to claim 8, wherein the plate presents a thickness along the first direction and the value of the thickness falling into an interval from 0.8 to 1.5 mm.

10. The sterilization machine according to claim 5, wherein the plate comprises an external housing at least partially realized in stainless steel.

11. The sterilization machine according to claim 5, wherein the plate comprises an external housing at least partially realized in stainless steel.

12. The sterilization machine according to claim 1, wherein the isolation chamber comprises a plurality of walls delimiting the inner space;
wherein the plurality of walls comprises two lateral walls, the two lateral walls being distanced from one another along a horizontal axis, which is operatively transversal to the gravity, the lateral walls being transversal to the horizontal axis;
the second direction is parallel to the horizontal axis;
for each cart, the actuation unit is configured in such a manner to control the second position component maintaining the cart distanced from the lateral walls independently from the other carts.

13. The sterilization machine according to claim 1, wherein:
the at least one portion of the advancement path comprises at least a curved sector;
for each cart, the actuation unit is configured to control the electromagnetic field in such a manner to modify and/or control a roll inclination and/or a pitching inclination of the cart during advancement along the curved sector.

14. The sterilization machine according to claim 1, wherein:
the machine is void of a mechanical guide for guiding by means of mechanical contact advancement of the carts along the advancement path in such a manner that the advancement path is solely defined by the control of the electromagnetic field.

15. The sterilization machine according to claim 1, comprising a cooling device;

wherein the isolation chamber and the actuation unit are distanced from one another along the first direction so as to define an interspace interposed between the isolation chamber and the actuation unit;

wherein the cooling device is configured to generate a cooling flow within and through the interspace.

16. The sterilization machine according to claim 1, wherein the actuation unit is defined by or comprises a planar motor.

* * * * *